US009664655B2

(12) United States Patent
Riviello

(10) Patent No.: US 9,664,655 B2
(45) Date of Patent: May 30, 2017

(54) ELECTROLYTIC ELUENT RECYCLE DEVICE, APPARATUS AND METHOD OF USE

(71) Applicant: Dionex Corporation, Sunnyvale, CA (US)

(72) Inventor: John M. Riviello, Los Gatos, CA (US)

(73) Assignee: Dionex Corporation, Sunnyvale, CA (US)

( * ) Notice: Subject to any disclaimer, the term of this patent is extended or adjusted under 35 U.S.C. 154(b) by 656 days.

(21) Appl. No.: 14/093,691

(22) Filed: Dec. 2, 2013

(65) Prior Publication Data

US 2014/0083854 A1    Mar. 27, 2014

Related U.S. Application Data

(63) Continuation of application No. 12/360,802, filed on Jan. 27, 2009, now Pat. No. 8,597,571.

(60) Provisional application No. 61/062,747, filed on Jan. 28, 2008.

(51) Int. Cl.
| | | |
|---|---|---|
| *G01N 30/02* | (2006.01) | |
| *G01N 30/26* | (2006.01) | |
| *G01N 30/96* | (2006.01) | |
| *B01D 15/16* | (2006.01) | |
| *B01D 15/36* | (2006.01) | |

(52) U.S. Cl.
CPC ............. *G01N 30/96* (2013.01); *B01D 15/16* (2013.01); *B01D 15/36* (2013.01); *G01N 2030/965* (2013.01)

(58) Field of Classification Search
CPC ........ G01N 30/02; G01N 30/26; G01N 30/34; G01N 30/342; G01N 30/345
See application file for complete search history.

(56) References Cited

U.S. PATENT DOCUMENTS

| | | |
|---|---|---|
| 5,045,204 A | 9/1991 | Dasgupta et al. |
| 6,027,643 A | 2/2000 | Small et al. |
| 6,508,985 B2 | 1/2003 | Small et al. |
| 7,329,346 B2 | 2/2008 | Liu et al. |
| 7,473,354 B2 | 1/2009 | Liu et al. |
| 2003/0127392 A1 | 7/2003 | Srinivasan et al. |
| 2003/0132163 A1 | 7/2003 | Srinivasan et al. |
| 2006/0057733 A1 | 3/2006 | Liu et al. |
| 2006/0186046 A1 | 8/2006 | Liu et al. |
| 2006/0231404 A1 | 10/2006 | Riviello |

(Continued)

FOREIGN PATENT DOCUMENTS

| | | |
|---|---|---|
| EP | 0442224 A2 | 8/1991 |
| EP | 1867384 A1 | 12/2007 |
| JP | 5-18948 | 1/1993 |

(Continued)

OTHER PUBLICATIONS

Rabin, S., J. Stillian, et al.. New membrane-based electrolytic suppressor device for suppressed conductivity detection in ion chromatography. *Journal of Chromatography*, 640 (1993) 97-109.

*Primary Examiner* — Jan Ludlow

(57) ABSTRACT

Electrolytic eluent recycle systems for ion chromatography using a multi-channel electrolytic ion exchange device which integrates suppression, eluent generation, and eluent recycle. The systems recycle the eluent into the analytical system without passing the eluent through the electrode chambers. Also, such systems with a channel for electrolytic removal of ions from the suppression effluent before recycle.

13 Claims, 9 Drawing Sheets

CIRA Anion C Eluent Recycle

(56) References Cited

U.S. PATENT DOCUMENTS

| | | | |
|---|---|---|---|
| 2008/0116139 A1 | 5/2008 | Liu et al. | |
| 2009/0101582 A1 | 4/2009 | Liu et al. | |

FOREIGN PATENT DOCUMENTS

| | | | |
|---|---|---|---|
| JP | 2002509238 A | 3/2002 | |
| JP | 2004508540 A | 3/2004 | |
| JP | 2005-515055 | 5/2005 | |
| JP | 2005538382 A | 12/2005 | |
| WO | WO99 44054 A1 | 9/1999 | |
| WO | WO02 04940 A1 | 1/2002 | |
| WO | WO2006 113306 A2 | 10/2006 | |

Figure 1. CIRA Anion C Eluent Recycle
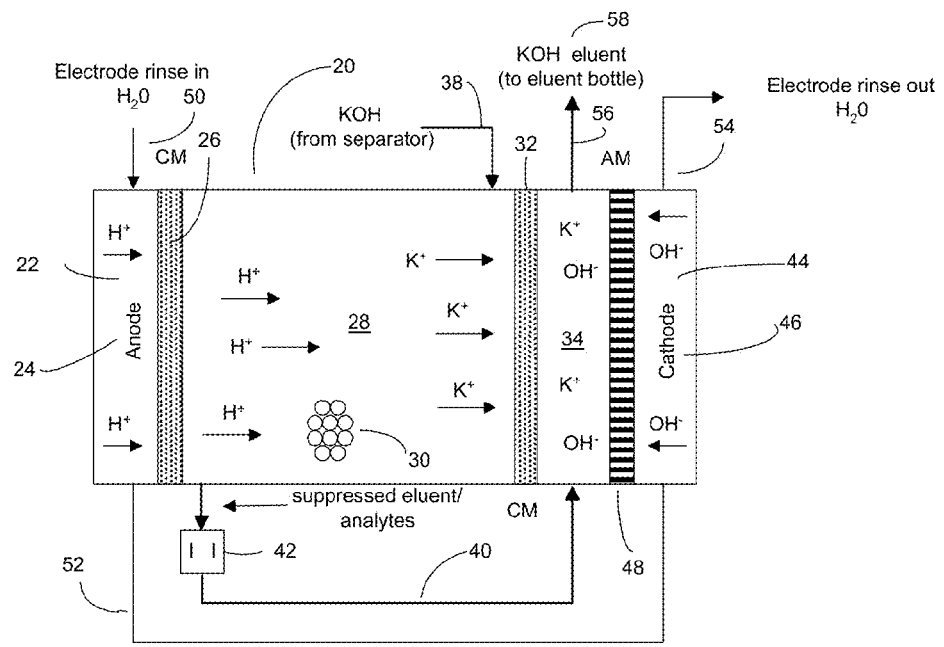
Figure 2. CIRA Anion X Eluent Recycle
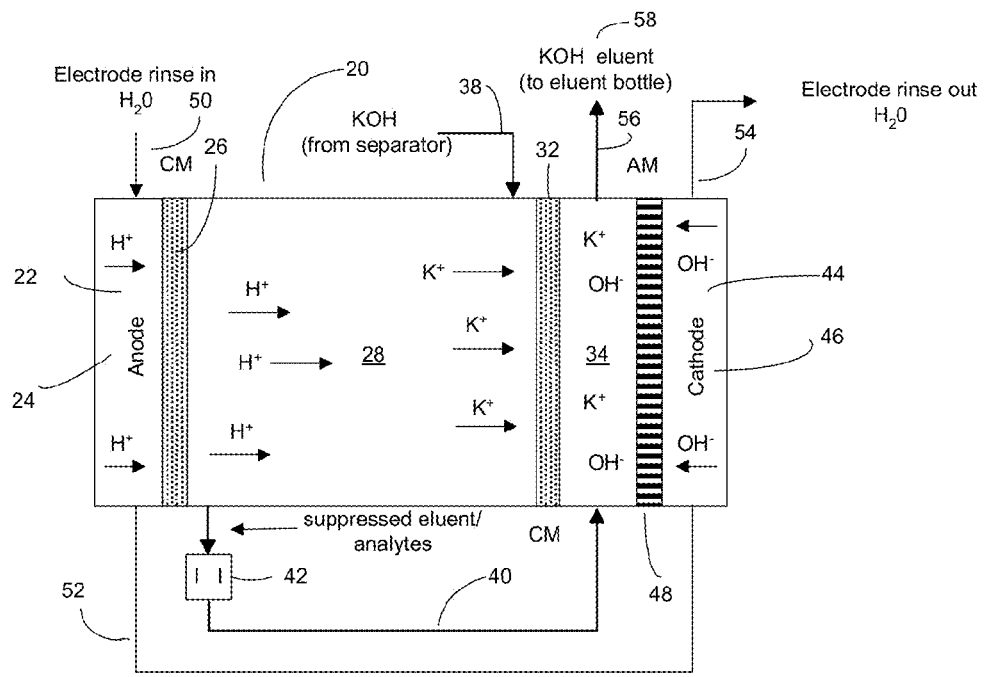

Figure 3. CIRA Anion A Eluent Recycle
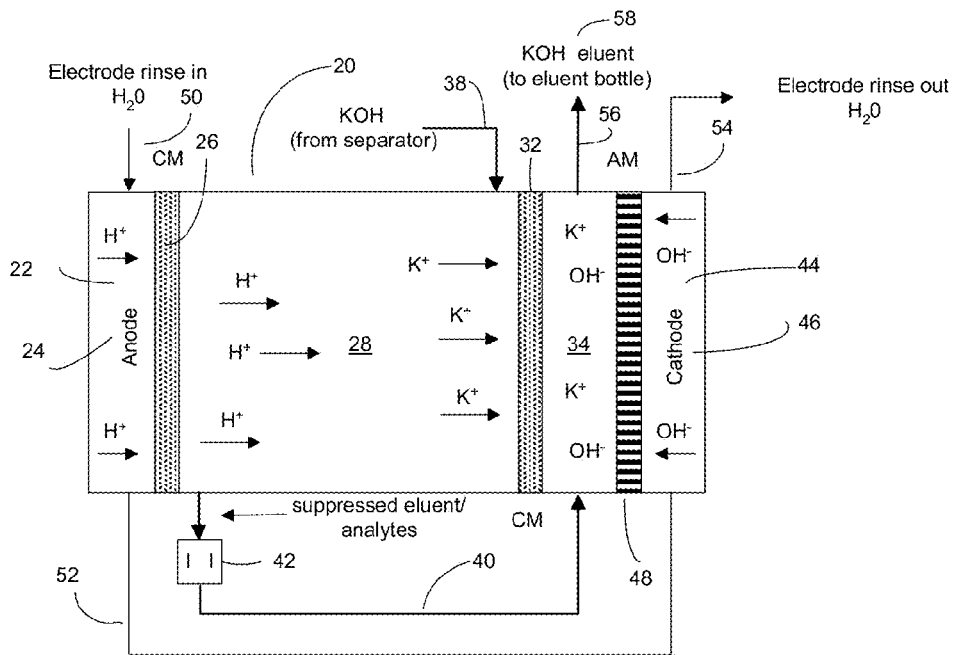
Figure 4. CIRA Anion A Eluent Recycle with Integrated Anion Removal
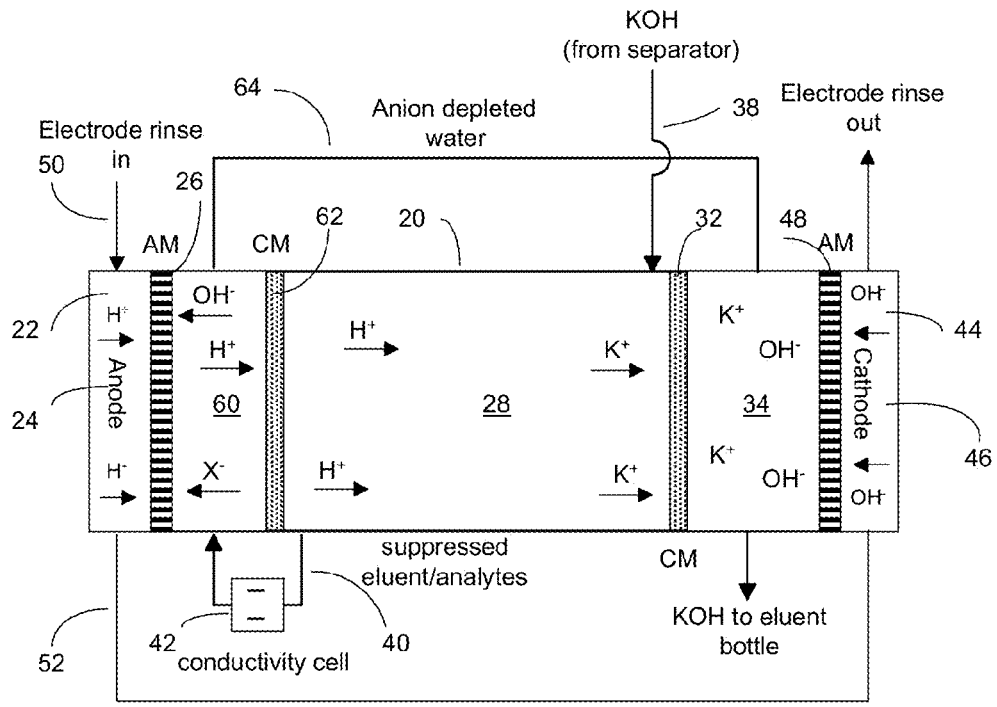

Figure 5. CIRA Anion X Eluent Recycle with Integrated Anion Removal
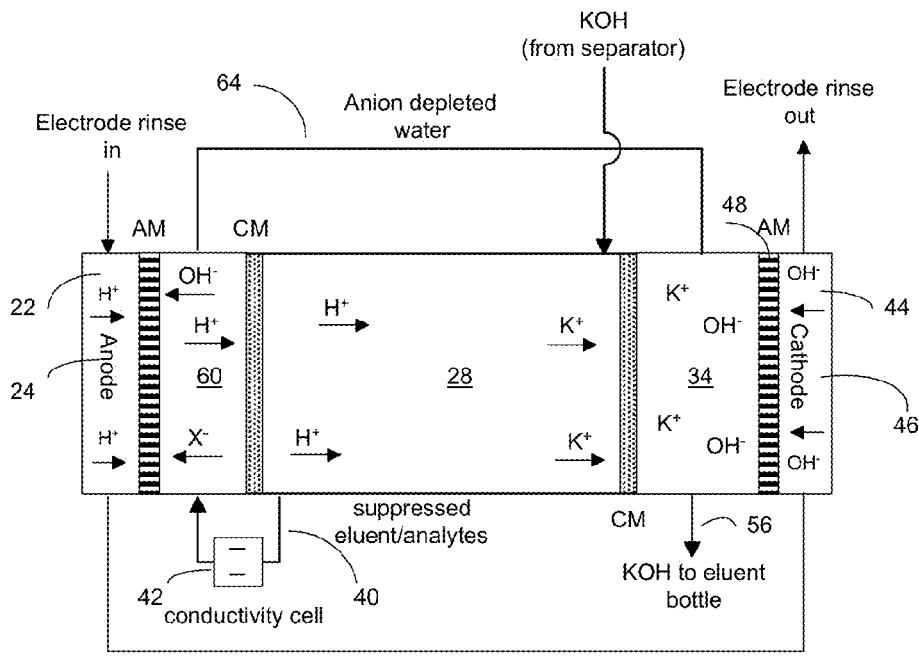
Figure 6. CIRA Anion A Eluent Recycle with Integrated Anion Removal
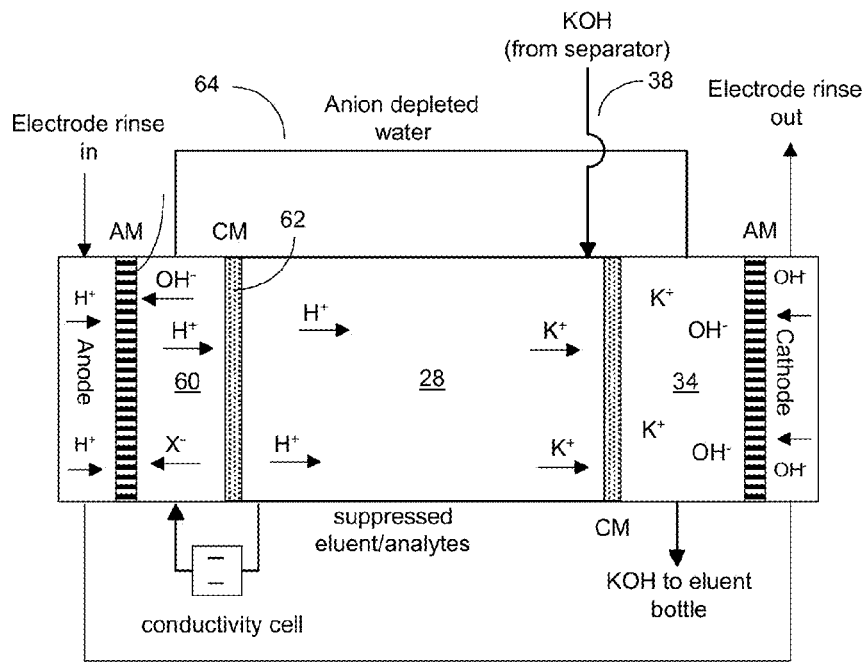

Figure 7. CIRA Cation A Eluent Recycle
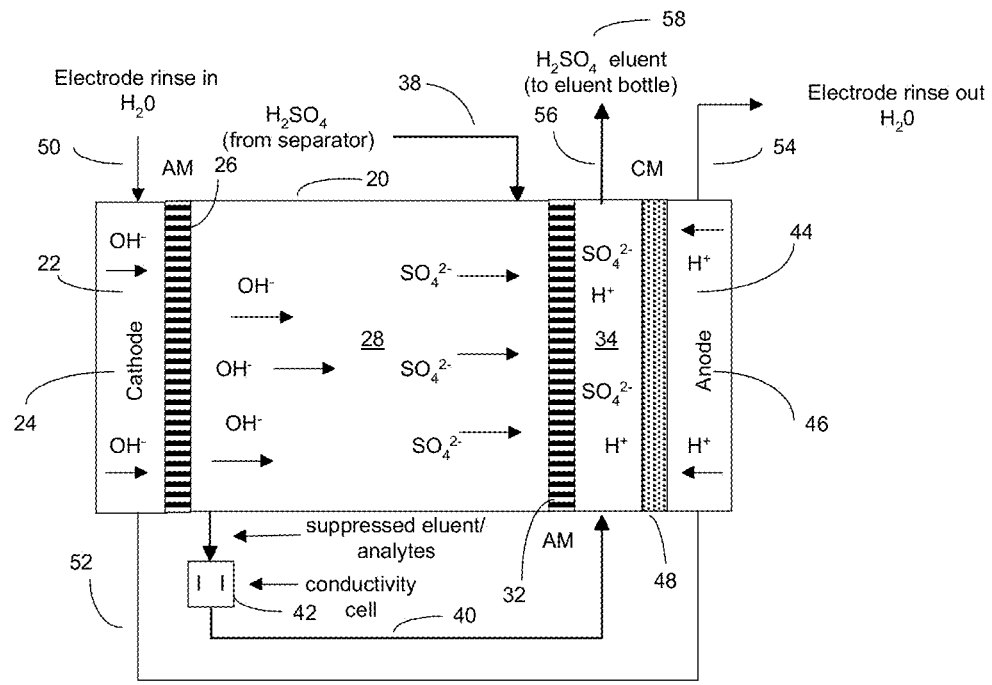
Figure 8. CIRA Cation X Eluent Recycle
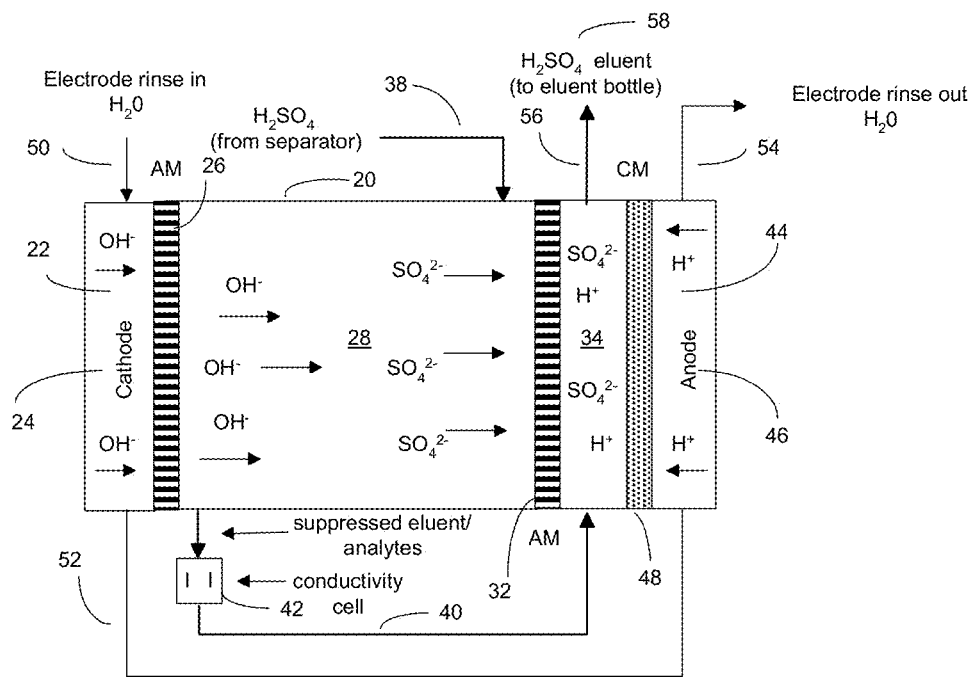

Figure 9. CIRA Cation C Eluent Recycle
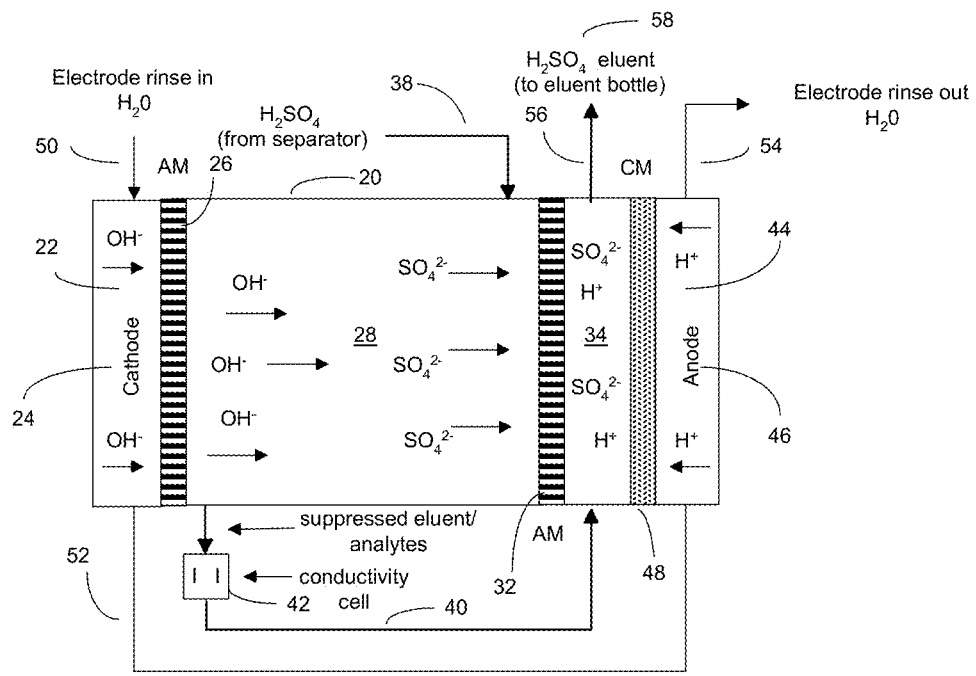
Figure 10. CIRA Cation A Eluent Recycle with Integrated Anion Removal
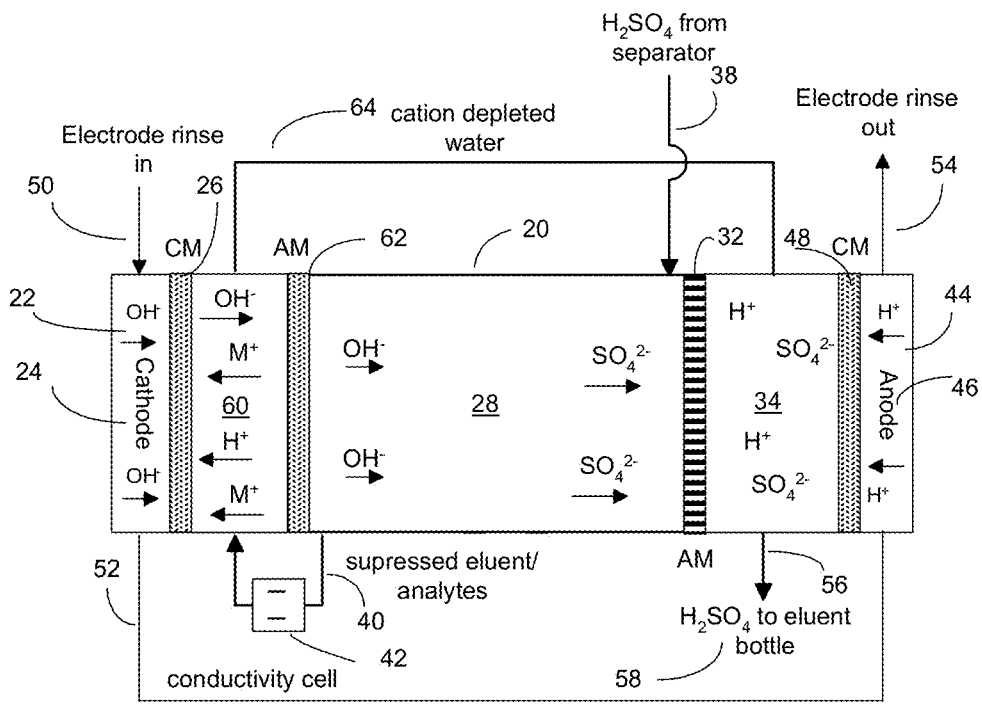

Figure 11. CIRA Cation AX Eluent Recycle with Integrated Anion Removal
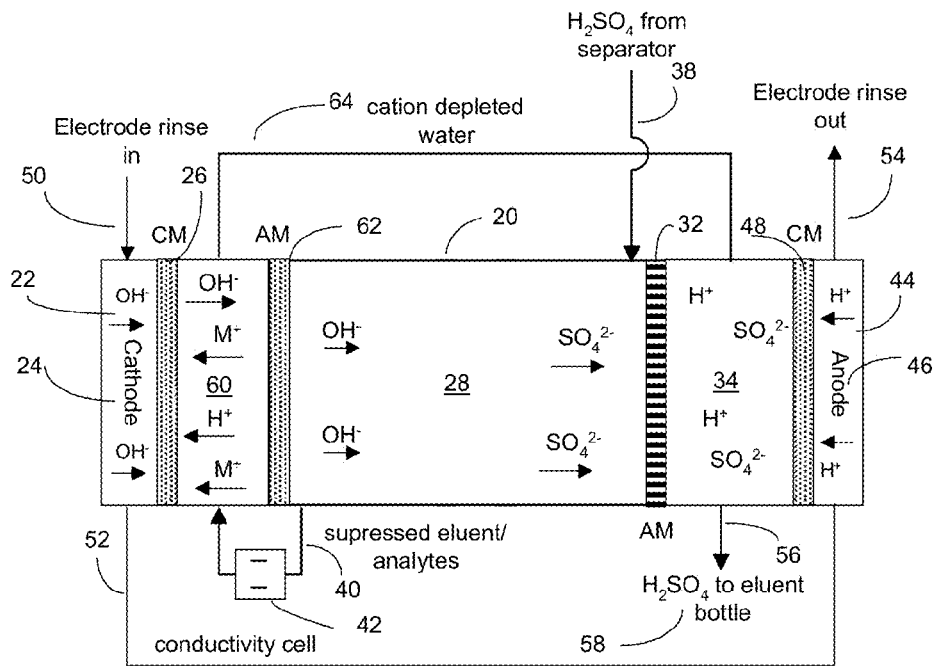
Figure 12. CIRA Cation XX Eluent Recycle with Integrated Anion Removal
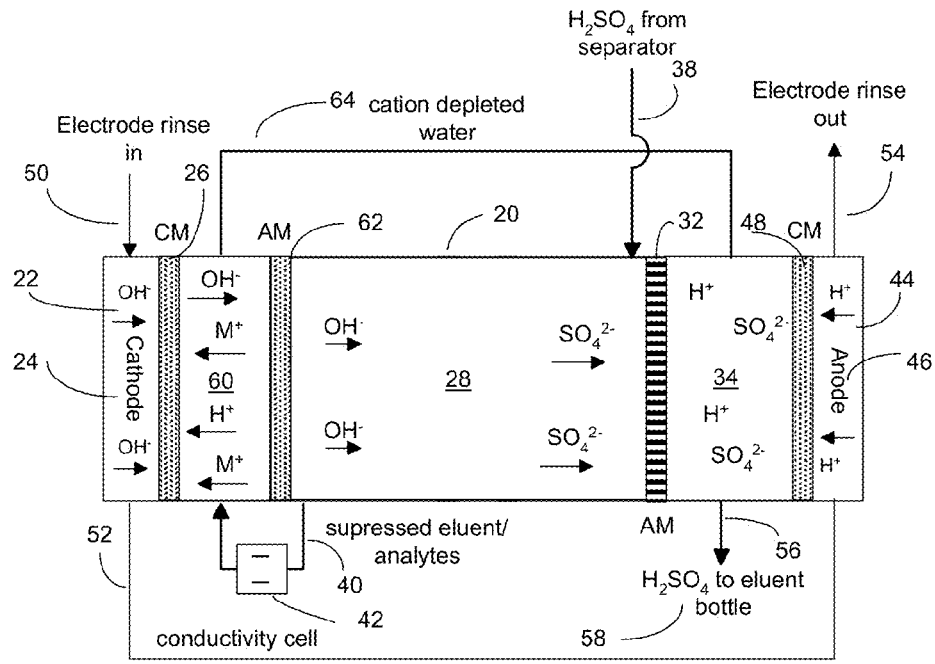

Figure 13. Anion Chromatography with Integrated Suppression and Eluent Generation
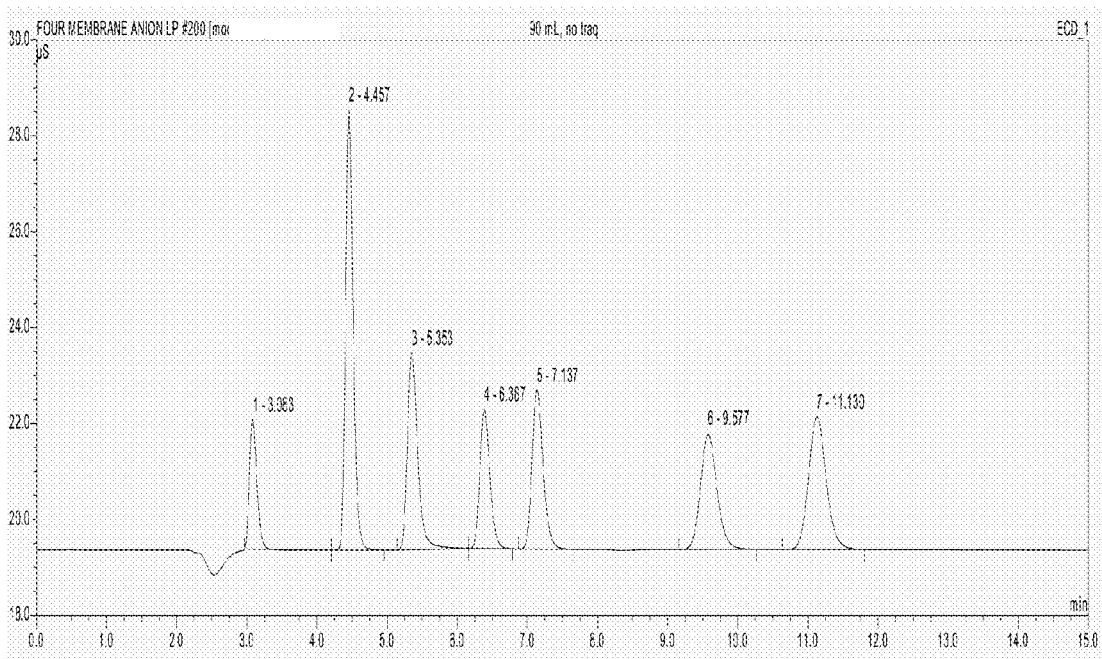
Figure 14. Retention Time Trend for Anion Chromatography with Integrated Suppression and Eluent Generation (26 cycles)
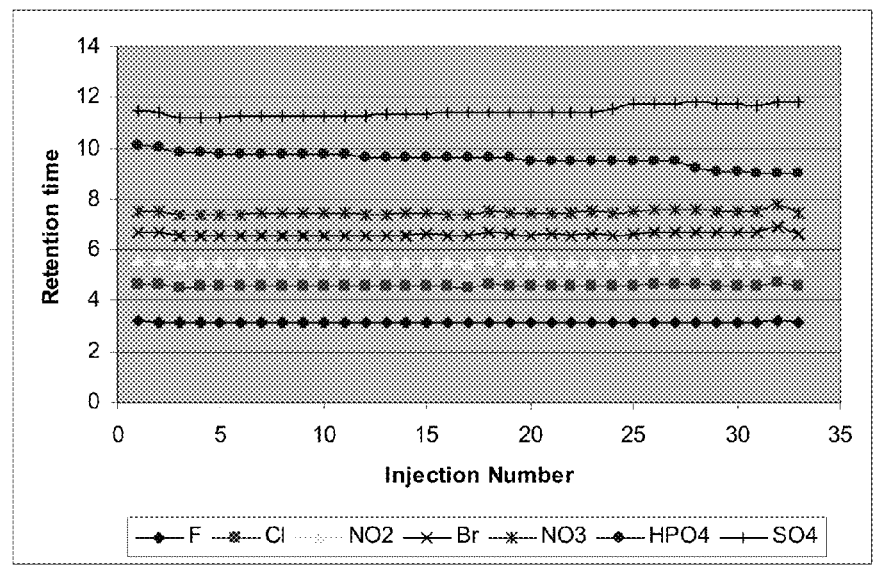

Figure 15. Anion Chromatography with Integrated Suppression and Eluent Generation (9 cycles)
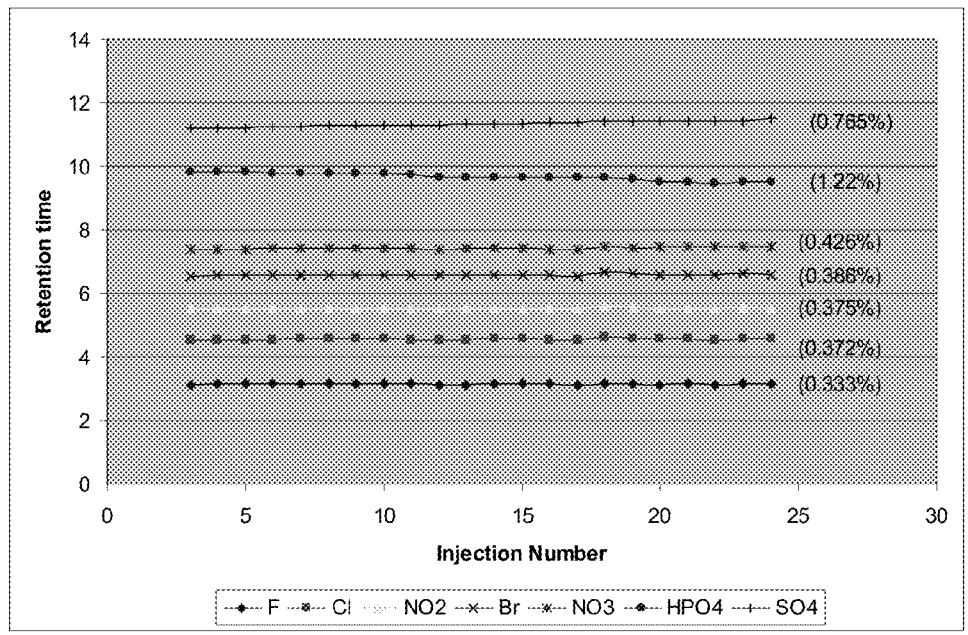
Figure 16. Cation Chromatography with Integrated Suppression and Eluent Generation (overlay of eight runs)
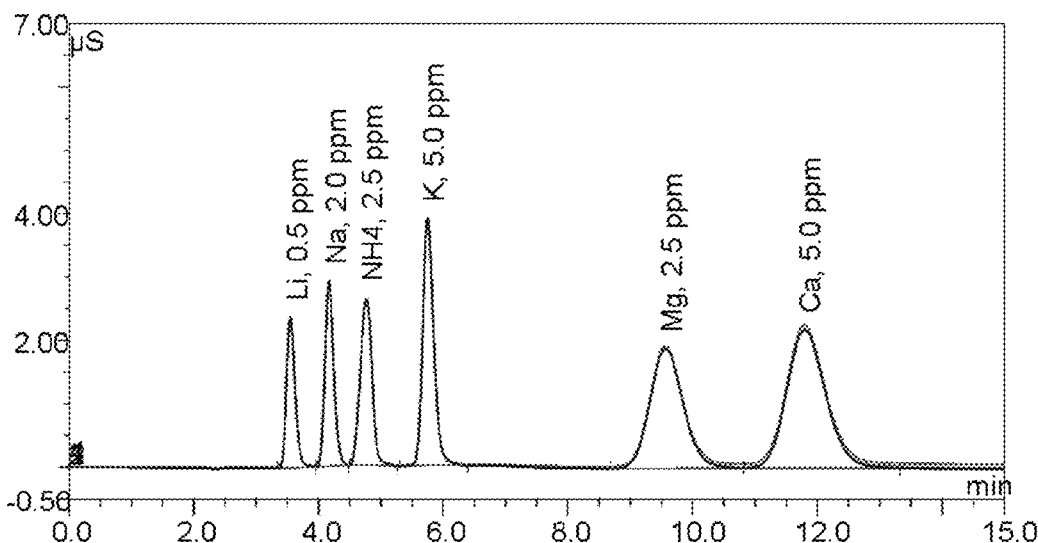

Figure 17. Retention Time Trend for Cation Chromatography with Integrated Suppression and Eluent Generation (22 cycles)
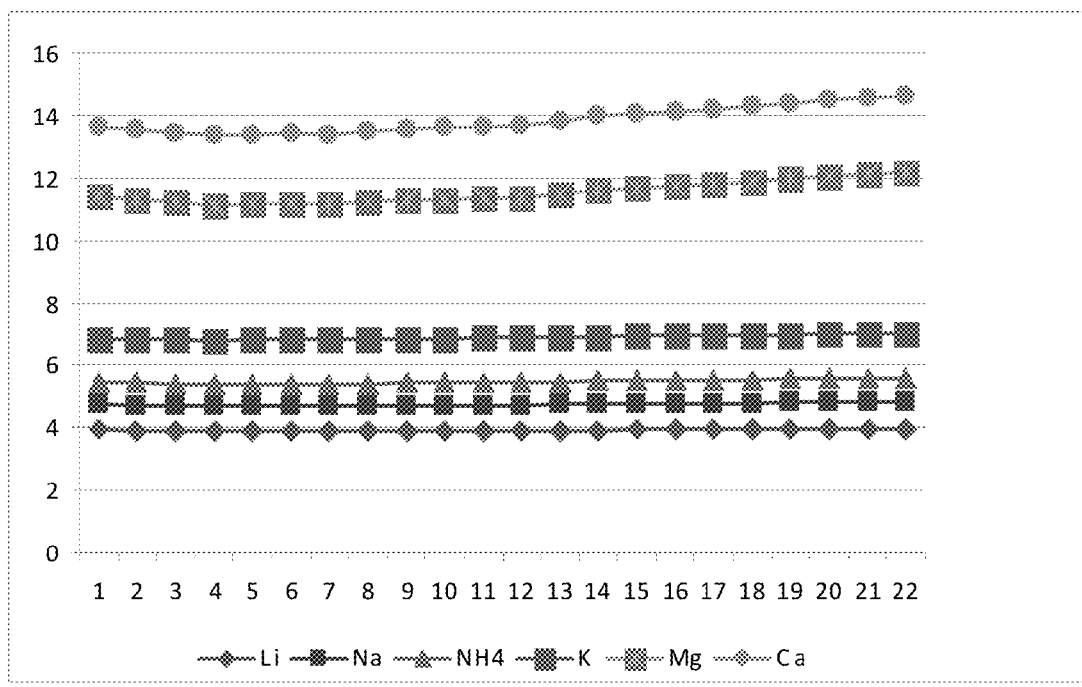

ELECTROLYTIC ELUENT RECYCLE DEVICE, APPARATUS AND METHOD OF USE

CROSS-REFERENCE TO RELATED APPLICATIONS

This application is a Continuation under 35 U.S.C. §120 and claims the priority benefit of co-pending U.S. Non-Provisional application Ser. No. 12/360,802, filed on Jan. 27, 2009, entitled "Electrolytic Eluent Recycle Device, Apparatus And Method of Use," which claims the priority benefit to U.S. Provisional Application No. 61/062,747 filed on Jan. 28, 2008, entitled "Electrolytic Eluent Recycle Device, Apparatus And Methods of Use," the entire disclosure of which is incorporated by reference.

BACKGROUND OF THE INVENTION

Trovion, a company now located in Campbell, Calif., has developed, manufactured and marketed electrolytic ion exchange devices for analytical scale water purification. The Trovion CIRA products are designed to integrate into analytical instrumentation with the product water flow rate being compatible with instrumentation.

In the Trovion electrolytic ion exchange devices, the product water, or analytical stream, never passes through the electrode chambers. As a result, the product water or sample stream is not contaminated with electrolysis by-products such as oxygen, hydrogen, ozone and hydrogen peroxide. Since ozone and hydrogen peroxide can damage ion exchange materials, minimizing contact of critical ion exchange components with these oxidizers is advantageous.

In US Patent Application US20060231404, an electrolytic suppressor and eluent purifier is disclosed in which the electrode chambers are isolated from the analytical or waste stream (resulting from the feed). For the suppression of hydrochloric acid, no damage to the ion exchange materials was observed since chloride is not received into the anode compartment, but instead is received into a non-electrolytic central mixed bed waste chamber.

In US Patent Application US20060186046, an ion chromatography system using catalytic gas elimination combined with eluent recycle is described. In this system, electrolytic suppressors are used and the recycled eluent is recovered in the electrode chambers. Since the electrode chambers produce hydrogen and oxygen, catalytic elimination of the hydrogen and oxygen gases is used. The catalytic recombination of oxygen and hydrogen to water eliminates problems associated with dissolved gases in the eluent stream and aids in reducing electrolytic by products such as ozone and hydrogen peroxide.

SUMMARY OF THE INVENTION

One embodiment of the invention is an integrated suppressor and eluent generator apparatus for ion chromatography comprising a suppressor chamber comprising ion exchange material and including an inlet and an outlet, a first electrode chamber comprising a first electrode and including an inlet and an outlet, a second electrode chamber comprising a second electrode and including an inlet and an outlet, an eluent generator chamber comprising flow-through ion exchange material and including an inlet and an outlet, a first barrier preventing significant liquid flow, but permitting transport of ions of only one charge, positive or negative, disposed between the eluent generator chamber and the second electrode chamber, a second barrier preventing significant liquid flow, but permitting transport of ions of only one charge, positive or negative, disposed between the suppressor chamber and the eluent generator chamber, an eluent recycle conduit providing fluid communication, directly or indirectly, between the suppressor chamber and the eluent generator chamber, and an electrode rinse conduit disposed between first and second electrode chambers isolated from said eluent recycle conduit.

Another embodiment is an integrated suppressor and eluent generator apparatus for ion chromatography comprising a suppressor chamber comprising ion exchange material and including an inlet and an outlet, a first electrode chamber comprising a first electrode and including an inlet and an outlet, a second electrode chamber comprising a second electrode and including an inlet and an outlet, an eluent generator chamber comprising flow-through ion exchange material and including an inlet and an outlet, a first barrier preventing significant liquid flow, but permitting transport of ions of only one charge, positive or negative, disposed between the eluent generator chamber and the second electrode chamber, a second barrier preventing significant liquid flow, but permitting transport of ions of only one charge, positive or negative, disposed between the suppressor chamber and the eluent generator chamber, a third barrier preventing significant liquid flow, but permitting transport of ions of only one charge, positive or negative, disposed between the first electrode chamber and the suppressor chamber, an ion removal chamber comprising ion exchange material, a fourth barrier preventing significant liquid flow, but permitting transport of ions of only one charge, positive or negative, disposed between the first electrode chamber and the ion removal chamber, and an eluent recycle conduit providing fluid communication between the suppressor chamber and the eluent generator chamber and comprising the ion removal chamber and an eluent recycle conduit portion disposed between the ion removal chamber and the eluent generator chamber.

A further embodiment is an ion chromatography method using an integrated suppressor and eluent generator chamber apparatus for ion chromatography comprising a suppressor chamber comprising ion exchange material and including an inlet and an outlet, a first electrode chamber comprising a first electrode and including an inlet and an outlet, a second electrode chamber comprising a second electrode and including an inlet and an outlet, an eluent generator chamber comprising flow-through ion exchange material and including an inlet and an outlet, a first barrier preventing significant liquid flow, but permitting transport of ions of only one charge, positive or negative, disposed between the eluent generator chamber and the second electrode chamber, and a second barrier preventing significant liquid flow, but permitting transport of ions of only one charge, positive or negative, disposed between the suppressor chamber and the eluent generator chamber. The method comprises flowing an eluent stream comprising separated ionic species of one charge, positive or negative, through the suppression chamber to suppress the eluent, recycling the suppressed eluent from the suppressor chamber, directly or indirectly, to the eluent generator chamber, passing a current between the first and second electrodes through the suppressor chamber and eluent generator chamber, during suppression, for suppression and eluent generation, and flowing an aqueous rinse solution through the first and second electrode chambers and between them.

Another embodiment comprises an ion chromatography method using an integrated suppressor and eluent generator apparatus for ion chromatography comprising a suppressor chamber comprising ion exchange material and including an inlet and an outlet, a first electrode chamber comprising a first electrode and including an inlet and an outlet, a second electrode chamber comprising a second electrode and including an inlet and an outlet, an eluent generator chamber comprising flow-through ion exchange material and including an inlet and an outlet, a first barrier preventing significant liquid flow, but permitting transport of ions of only one charge, positive or negative, disposed between the eluent generator chamber and the second electrode chamber, a second barrier preventing significant liquid flow, but permitting transport of ions of only one charge, positive or negative, disposed between the suppressor chamber and the eluent generator chamber, a third barrier preventing significant liquid flow, but permitting transport of ions of only one charge, positive or negative, disposed between the first electrode chamber and the suppressor chamber, an ion removal chamber comprising ion exchange material, and a fourth barrier preventing significant liquid flow, but permitting transport of ions of only one charge, positive or negative, disposed between the first electrode chamber and the ion removal chamber. The method comprises flowing an eluent stream comprising separated ionic species of one charge, positive or negative, through the suppression chamber to suppress the eluent, flowing the suppressed eluent from the suppressor chamber, directly or indirectly to the ion removal chamber and then to the eluent generator chamber, and passing a current between the first and second electrodes through the suppressor chamber, ion removal chamber, and eluent generator chamber, during suppression, for suppression, removal of ions in the ion removal chamber, and for eluent generation.

BRIEF DESCRIPTION OF THE DRAWINGS

FIGS. 1-12 are schematic representations of different integrated devices according to the invention.

FIGS. 13-17 depict experimental results using selected integrated devices of one of FIGS. 1-12.

DETAILED DESCRIPTION OF THE INVENTION

Electrolytic devices are disclosed in which the analytical stream (sample-containing eluent) does not pass through the electrode chambers. In all embodiments, a separate liquid flow is used for the electrode chambers. Some details of the construction, materials, operation and ion movement in the electrolytic device disclosed herein can be found in US patent application US20060231404.

The invention relates to improvements in integrated devices for eluent suppression and generation of eluents which can be used as the eluent (e.g. an acid or a base) for sample ions of one charge, positive or negative, to be chromatographically separated in an ion chromatograph (IC) system. Integrated devices which combine suppression with other operations are disclosed in U.S. Pat. Nos. 6,027,643 and 6,508,985; and in US Patent Applications US20060231404 and US20060186046, collectively "the prior art integrated device publications," and incorporated by reference for their disclosures of operation and construction, including details of suitable barrier and ion exchange materials.

The term "ion exchange materials" refers to ion exchange resins, e.g. ion exchange particles in an ion exchange particle bed, ion exchange fibers, ion exchange screens, or ion exchange monoliths. Typically, one of two types of ion exchange materials are used, anion exchange materials and cation exchange materials (i.e. ones with anion and/or cation exchangeable ions) such as disclosed in the prior art integrated device publications. Anion and cation exchange materials may be mixed to produce a mixed ion exchange material, e.g. in a mixed packed bed of anion and cation particles. Typically, the cation exchange material is a strong acid ion exchanger, i.e., a material containing sulfonic acid groups, and the anion exchange material is a strong base ion exchange containing quaternary amine groups. Preferably, the ion exchange materials are conductive so that ions may migrate through the ion exchange material towards the respective electrodes.

The invention uses a number of barriers which prevent significant liquid flow but which permit the transport of ions of only one charge, positive or negative, preferably through exchangeable ions on the barriers. Suitably such barriers are ion exchange membranes of one of two types, anion or cation exchange (i.e. ones with exchangeable anions or cations as disclosed in the prior art integrated device publications). These ion exchange membranes typically have strong basic or strongly acidic functional groups. An anion exchange membrane will transport only anions through the membrane, while the membrane prevents the bulk flow of liquid from one side of the membrane to the other. A cation exchange membrane will transport only cations through the membrane, while the membrane prevents the bulk flow of liquid from one side of the membrane to the other. Thus, preferably the membranes are conductive so that ions may migrate through the ion exchange membrane towards their respective electrodes. The invention will be described using ion exchange membranes as such barriers.

Anion Analysis Using the Device of FIG. 1.

FIG. 1 shows one embodiment of a device to be used for anion analysis. The integrated suppressor and eluent generator device 20 has four discrete chambers. It includes a first electrode chamber in the form of an anode chamber 22 containing an anode electrode 24, defined on one side by a cation exchange membrane 26 or connector (CM), separating the anode chamber 22 from suppression chamber 28. Suppression chamber 28 may be filled with a strong cation exchange material (e.g. Dowex 50WX8 cation exchange resin in a packed bed 30). A cation exchange membrane 32 or connector (CM) (of the same charge, positive or negative, as membrane 26) separates suppression chamber 28 from an eluent generator chamber 34. (The eluent generator generates a base, KOH as illustrated, to replenish part or all of the KOH eluent to be supplied to a chromatographic separator.) Chamber 34 is also referred to as a receiving chamber since it "receives" the eluent.

As shown in FIG. 1 for anion analysis, suppressor chamber 28, suitably containing high capacity cation exchange in a packed bed, is used to electrolytically suppress the eluent, illustrated as KOH, fed to chamber 28 from a chromatography separator (not shown) in line 38. The suppressed eluent ions (illustrated as $K^+$) are transmitted across cation exchange membrane 32 and received into chamber 34 in which eluent, e.g. KOH, is generated suitably for use as the eluent feed in line 38 to suppressor chamber 28. The chamber may contain ion exchange material having exchangeable cations or anions, or a mixture, (e.g. cation, anion or a mixture of anion and cation ion exchange resin particles in a bed). In this configuration, the device could be used for integrated suppression and eluent generation.

More specifically, as illustrated for anion analysis in FIG. 1, the eluent (an aqueous solution of KOH) flows in line 38 from a chromatographic separator (e.g. a chromatography column in which ions of one charge, positive or negative, are separated) to the inlet of suppressor chamber 28. Solution flowing through the suppressor chamber 28 flows in line 40 to the inlet of chamber 34 in which eluent is electrolytically generated. Between the outlet of suppressor chamber 28 and the inlet of chamber 34, the separated ions in line 40 are detected, e.g. in conductivity cell 42 in line 40.

An electrode chamber 44 contains an electrode 46 which is connected with electrode 24 to a power supply so that electrodes 24 and 46 are of opposite charge and a current is passed between the electrodes through all barriers and chambers of the device. As illustrated, electrode 46 is a cathode. Electrodes 24 and 46 may be flow-through electrodes or may be disposed in chambers 22 and 44, preferably parallel to liquid flow, with clearance for liquid flow. Electrode 46 is separated from chamber 34 by barrier 48 illustrated as an anion exchange membrane of opposite charge to cation exchange membrane 26 adjacent to electrode chamber 24.

An aqueous rinse water solution flows in line 50 into chamber 24 and out recycle line 52 to electrode chamber 44 and may flow in line 54 to waste. In an alternative, not shown, the rinse water may flow in the opposite direction between chambers 34 and 44. The rinse water is isolated from eluent flow. An advantage of a single recycle stream flowing sequentially between the electrode chambers versus flowing in parallel, is that the flow rate is equal in both electrode chambers.

Eluent solution (e.g. KOH) generated in chamber 34 is recycled in line 56 to an eluent reservoir (not shown) for use as all or part of the eluent to be supplied with the sample analytes to a chromatography column, not shown, for analyte separation and subsequent flow in line 38 to suppressor chamber 28.

Eluent generation in chamber 34 is performed by the electrolytic reactions illustrated in the prior art integrated device publications except that the electrodes are isolated from eluent flow, e.g. by membrane 48 which isolates electrode 46 from the chamber 34 in which eluent, e.g. KOH, is generated. Thus, the $H_2$ and $O_2$ gases generated at the electrodes are substantially isolated from chamber 34

Since the analytical stream (suppressed eluent) flowing in line 40, chamber 34, and line 56 never passes through the electrode chambers, the recycled generated eluent in line 56 will not contain oxygen, hydrogen and should not have appreciable concentrations of electrochemical by-products. A separate liquid flow is passed through the electrode chambers and in recycle line 52 which is isolated from the eluent stream. The electrode wash liquid typically is deionized water and serves as a source of water for electrolysis to produce hydronium at the anode and hydroxide at the cathode. The electrode rinse solution could be recycled.

In the device of FIG. 1, analyte anions will be present in the recycled eluent, but no hydrogen, oxygen, ozone or hydrogen peroxide. Over time, the analyte anions will accumulate in the recycled eluent in line 58 which can compromise performance.

For anion analysis, an anion trap column (not shown) placed in line 40 between the conductivity cell 42 and the eluent generation chamber 34 would remove the trace anions. This anion trap column could contain high capacity anion exchange resin material, e.g. in a packed bed, so that the lifetime of the trap could be very long. In addition to removing analytes form the recycled eluent, the trap column could also be designed to trap anionic oligomers leaching from the sulfonated cation exchange materials of the suppression chamber 28 and chamber 34.

For cation analysis, the polarity of all elements, e.g. the membranes and ion exchange materials, are reversed.

In FIG. 2, a device similar to that of FIG. 1 is illustrated with like parts designated with like numbers. The cation exchange material of the eluent chamber 34 is replaced with a composite (mixture) of anion and cation exchange materials (i.e. ones with anion and cation exchangeable ions). In this configuration, the anion exchange material of eluent chamber 34 can retain the analyte anions as well as anionic oligomer leach from the suppression chamber. Fully sulfonated cation exchange materials are known to leach anionically charged (typically sulfonated) material which are oligomers that result form sulfonation or incomplete polymerization. These anionic oligomers will bind substantially irreversibly to anion exchange materials. Thus, the anion exchange material in eluent generation chamber 34 will prevent contamination of the analytical anion separator column by the anionic leach from the suppression chamber 28. The anion exchange capacity in the eluent chamber 34 should be high enough so that the recycled eluent, water splitting or electrophoretic displacement will not result in a significant concentration of the analyte in the recycled eluent. The anion exchange capacity in eluent generation chamber 34 will also act to trap the analytes (sample anions). The anion capacity and selectivity will be sufficient so that the eluent formed in the chamber can not displace the anions into the eluent. Water splitting will occur in the eluent chamber as a result of the intimate contact of anion and cation exchange material and the applied electric field. Water splitting can displace retained analytes from the anion resin of eluent generation chamber 34. If the anion capacity is sufficient, water splitting will not be able to displace a significant amount of the trapped analyte anions. In principle, this should eliminate the need for an external anion trap column.

In FIG. 3, like parts with FIG. 1 will be designated with like numbers. The eluent chamber 34 contains only anion exchange material. In this configuration, water splitting occurs only at the cation membrane 32—anion exchange interface 34 and retention of analyte anion and anionic oligomers leach should be complete as a result of the high capacity anion exchange material.

A potential complication of the devices in FIGS. 2 and 3 with carbonate eluent may result from the fact that the anion exchange material of the eluent chamber 34 will affect the ratio of carbonate/bicarbonate and hydroxide in the solution and anion exchange phase. When polarized, there will be a continuous flux of hydroxide from the cathode chamber into the eluent chamber. Thus, some time will be required for the recycled eluent to fully equilibrate with the anion exchange resin and the continuous flux of hydroxide.

Other configurations for anion analysis are shown in FIGS. 4, 5 and 6. Like parts with FIG. 1 will be designed with like numbers. The devices of FIGS. 4, 5 and 6 incorporate an integrated anion removal chamber 60 independent of chamber 34 on the anode side of the device for anion analysis. These devices are compatible with hydroxide, but not carbonate eluent, since the carbonate would be removed into the anode chamber along with the analyte.

In the devices of FIGS. 4-6, analyte anions are removed into the electrode rinse in anode chamber 22 and would flow in line 52 to cathode chamber 44 which could be drawn into chamber 34 across anion exchange membrane 48. Since the anionic analyte concentration will be low, this should not be a major issue. An anion trap column (not shown) external to the integrated device 20 upstream in the electrode rinse streams 50 and 52 would trap such analyte anions.

In the device of FIG. 4, an anion removal chamber 60 is integrated into the device, containing mixed bed material. Chamber 60 is disposed between anode chamber 22 and suppressor chamber 28. Here, suppressed eluent/analytes flows in line 40 from suppressor chamber 28 through conductivity cell 42 to ion removal chamber 60 which is bounded on the anode chamber 22 side by anionic membrane barrier 26. Cation exchange membrane barrier 62 separates ion removal chamber 60 from suppressor chamber 28. As illustrated, the analyte anions are transmitted across anion exchange membrane 26 toward anode 24. Thus, the solution exiting chamber 60 in line 64 has been purified of the analyte anions and is a pure water source for generation of eluent (KOH) in chamber 34.

As in the device of FIG. 1, a possible problem with the device of FIG. 4 is the potential for anionic oligomer from the cationic eluent chamber. A solution to this is shown in FIG. 5, where the eluent chamber 34 contains a mixed anion and cation exchange material. As in FIG. 2, the anion exchange material of the mixed exchange material in the eluent chamber will minimize anionic leach. Anionic oligomers, which are strongly retained by the anion exchangers, accumulate in the eluent chamber since anions are not removed in this chamber.

The device of FIG. 6 contains only anion exchange material in the eluent chamber 34. This configuration further minimizes the risk of anionic oligomers in the recycled eluent.

Most anion samples will contain alkali and alkaline-earth metals. These cations will accumulate in the recycled eluent causing adverse chromatographic effects such as poor peak symmetry, reduced peak response and poor recovery. In addition, retention times may be affected since the carbonate-bicarbonate ratio will be changed as the cations accumulate in the recycled eluent.

For samples high in cations such as sodium, potassium, ammonium, calcium and magnesium, the sample cations may need to be removed prior to injection of sample in the eluent for chromatographic analysis in the separator which flows in line 38 to suppressor chamber 28. For manual sample injection, this could be accomplished using a cation exchange column in the hydronium form for sample pre-treatment prior to separation. When using an autosampler, a cation trap column (hydronium form) could be placed between the autosampler and an injection valve. The cation trap column capacity could be designed to last as long as the recycled eluent, and would be replaced with the eluent.

Electrode Rinse in Anion Analysis

The electrode rinse solution provides aqueous flow through the electrode chambers and when electrolyzed, provides hydronium and hydroxide for regeneration of the ion exchange materials. The electrode rinse could be delivered to the electrode chambers via a peristaltic pump and the electrode rinse could be recycled.

The electrolysis reaction produces oxygen and hydrogen gases. These gases must either be vented so they do not accumulate in the rinse container or recombined (using a platinum or palladium catalyst) to water. The simplest approach uses an open electrode rinse container which provides the required venting. It is also possible to separate the cathode and anode streams.

At the anode, ozone is produced and at the cathode, hydrogen peroxide. Both are these compounds are strong oxidizers and can attack not only the ion exchange materials, but can react with other ions forming anionic oxidizers such as hypochlorite and percarbonate.

By minimizing the production of hydrogen peroxide or by consuming it after production, the adverse effects of hydrogen peroxide can be minimized. Since hydrogen peroxide is not stable in base, the electrode rinse solution for anion analysis could be dilute sodium hydroxide. This should prevent the build-up of hydrogen peroxide in the recycled electrode rinse solution for anions For cation analysis in ion chromatography, an acid eluent such as sulfuric, nitric or methanesulfonic acid can be used and recycled using the devices shown in FIGS. 7-12. For FIGS. 7-12, like parts will be designated with like numbers as in FIGS. 1-6. In general, the cation analysis devices of FIGS. 7-12 have the same components as the anion analysis devices of FIGS. 1-6 except for a change of polarity of the analytes, reagents and charged components of the devices. Referring to FIGS. 7-9, for cation analysis, the suppression chamber 28 contains anion exchange resin and eluent generation chamber 34 contains anion, cation or a mixture of ion exchange materials. An external cation trap column, not shown, is preferably disposed in line 40 between the outlet of conductivity cell and eluent generation chamber 34 An advantage of the devices of FIGS. 7-12, is their compatibility with electrochemically active eluents such as nitric and hydrochloric acids. In a conventional electrolytic suppressor used in cation analysis, the eluent anion is removed into the anode chamber 44 (previously the cathode chamber). If the eluent anion is electroactive such as chloride, oxidation of the chloride to hypochlorite occurs. The hypochlorite will concentrate in the anion exchange material of the anode chamber causing degradation of the ion exchange material and subsequent failure of the suppressor. In the devices below, the eluent anion is not removed into the electrode chamber, but instead into the non-electroactive receiving chamber (eluent generation chamber).

As illustrated, sulfuric acid is used as an eluent. Chamber 34 in FIG. 7 contains only anion exchange material. The anion resin will be in the sulfate/bisulfate and hydroxide forms depending on the resin and applied current. To the extent that the anion resin is in the hydroxide form, degradation of the anion resin could occur resulting in trace amines and ammonia being added to the recycled eluent. This may cause an increase in background conductivity of the suppressed eluent. A solution to this problem is to replace the anion exchange resin of eluent generation chamber 34 with mixed bed resin, as shown in FIG. 8. Trace cations from the anion resin degradation as well as analyte cations, will be trapped for some period in the cation resin of the mixed bed.

The device of FIG. 9 replaces the mixed bed of eluent generation chamber 34 in FIG. 8 with cation resin. This eliminates the cationic degradation products of chamber 34 and may also trap any degradation products from suppression chamber 28 and will retain analyte cations for some period. Sulfonated anionic leach from the cation resin of the chamber (see FIG. 9) would be present in the eluent but then trapped by the anion resin of the suppression chamber.

In FIGS. 10, 11 and 12, a cation removal chamber 60 is added adjacent to the cathode 24 for continuous removal of cation analytes. Since the cation removal chamber 60 is continuously regenerated, an external trap cartridge may be eliminated. Any cationic degradation from the suppression chamber (amines and ammonia) should also be removed in the analyte removal chamber. Analyte cations are removed into cathode chamber 22 and the water exiting the analyte removal chamber 60 is deionized before entering eluent generation chamber 34. The analyte cations in the electrode rinse can be drawn into eluent generation chamber 34 from anode chamber 44. Since the analyte concentration will be low, this is not considered to be a major issue.

In FIGS. 10, 11 and 12, the eluent generation chambers contain anion resin, mixed bed resin and cation resin, respectively.

Counter Ion Effects in Cation Analysis

Each injection of a sample for cations analysis will introduce sample anion contaminants (counter-ions) into the system. One approach to the counter-ion problem is to restrict the use of the recycle approach to samples with low TDS (below 10 ppm). In this case, the sample anion contaminants may not present a problem during the lifetime of the recycled eluent.

In most samples, the sample anion contaminants will be the anions such as chloride and sulfate. These anions will accumulate in the recycled eluent in the acid from and will increase the acid eluent concentration causing a decrease in retention times. This could offset the decrease in the eluent concentration from dilution of the eluent by sample injection.

For samples high in anion contaminants such chloride or sulfate, it may be necessary to remove the sample anions prior to injection. For manual sample injection, this could be accomplished via an anion trap column in the hydroxide form. When using an autosampler, an anion trap column could be placed between the autosampler and an injection valve. The anion trap column capacity could be designed to last as long as the recycled eluent, and would be replaced with the eluent.

An alternative approach uses an electrolytic cation exchange device as the trap column. This could be a CIRA device (CIRA 10A) or a Dionex CR-ATC. With these devices, regeneration is continuous and the trap would not have to be replaced periodically.

Electrode Rinse for Cations

The electrode rinse for cations can not contain base since the cation of the base will be electrophoretically drawn into the eluent chamber. One proposed solution is to use water as the electrode rinse with an anion exchange cartridge in the hydroxide form. This should help degrade the hydrogen peroxide, but degradation of the hydroxide form resin will result in ammonia and amines.

In order to illustrate the present invention, the following non-limiting examples of its practice are set forth.

Example 1

Anion IC Using an Integrated Suppressor and Eluent Generator

An integrated suppressor and eluent generator device for anion IC (FIG. 1) was constructed using machined high density polyethylene hardware to retain the electrodes, membranes and resin. The internal flow dimensions of the suppression chamber were 0.40 cm in diameter and 3.81 cm in length. The internal flow dimensions of the eluent generation chamber were 0.40 cm in diameter and 1.27 cm in length.

The anode chamber contained a platinum gauze electrode (Unique Wire Weaving Inc, Hillside, N.J.). In contact with the anode and separating the anode chamber from the suppression chamber was a cation membrane (Electropure Excellion I-100, a product of Electropure Inc, Laguna Hills, Calif.). The suppression chamber was filled with cation exchange resin (DOWEX™ 50×4 (200 mesh), a product of the Dow Chemical Company, Midland, Mich.) in the hydronium form. A cation membrane (Electropure Excellion I-100 cation membrane, a product of Electropure Inc, Laguna Hills, Calif.) separated the suppression chamber from the eluent generation chamber.

The eluent generation chamber was filled with cation exchange resin (DOWEX™ 50×4 (200 mesh), a product of the Dow Chemical Company, Midland, Mich.) in the hydronium form. Separating the eluent generation chamber from the cathode chamber is anion membrane (Electropure Excellion 1-200 anion membrane, a product of Electropure Inc, Laguna Hills, Calif.) The cathode chamber contained platinum gauze electrodes (Unique Wire Weaving Inc, Hillside, N.J.). The cathode is in direct contact with the cation membrane and cathode chamber. A Dionex ATC3 anion trap column (not shown in FIG. 1) was placed between the conductivity cell outlet and the eluent generator chamber inlet chamber to trap the analyte anions from the suppressed eluent.

The device of FIG. 1 was tested using a Dionex DX500 Ion Chromatography system (a product of Dionex Corp, Sunnyvale, Calif.) consisting of a GP50 pump, CD25 conductivity detector and a LC30 chromatography oven. An eluent of 4.5 mM sodium carbonate and 1.4 mM sodium bicarbonate was pumped at a flow of 1.2 mL/min to a analytical anion exchange column (AG22/AS22 a product of Dionex Corp., Sunnyvale, Calif.) for separation of the sample anions. An Agilent E3611A DC power supply (Agilent Corp., Santa Clara, Calif.) was used to power the device of FIG. 1 at a constant current of 35 mA (approximately 30V). A peristaltic pump (MASTERFLEX LS, a product of the Cole-Parmer company, Vernon Hills, Ill.) was used to recycle deionized water at a flow rate of 2.0 mL/min to the anode chamber and then to the cathode chamber and then back to the deionized water container.

From the outlet of the analytical column, the eluent was directed to the inlet of the suppression chamber, out of the suppression chamber and to the conductivity cell, out of the conductivity cell and to the trap column and then to the eluent generation chamber. From the outlet of the generation chamber the eluent can be directed to waste (non-recycle mode) or back to the eluent container (recycle mode). FIG. 13 shows a chromatogram obtained with the system described above.

Table I shows retention times and chromatographic efficiencies for the common anions using the device of FIG. 1. The chromatographic efficiencies are comparable to those obtained with commercially available electrolytic suppressors.

TABLE I

Chromatographic Efficiency for Anion ER

| Peak | Name | RT min | Plates (ER) |
| --- | --- | --- | --- |
| 1 | fluoride. | 3.083 | 4986 |
| 2 | chloride | 4.457 | 11107 |
| 3 | nitrite | 5.353 | 8488 |
| 4 | bromide | 6.387 | 12149 |
| 5 | nitrate. | 7.137 | 12151 |
| 6 | phosphate | 9.577 | 9415 |
| 7 | sulfate. | 11.13 | 11081 |

Recycling an eluent volume of 500 mL, the retention time trend data in FIG. 14 was obtained. The data represents 26 complete recycle (regeneration) of the 500 mL of eluent.

This number of cycles is equivalent to operating the system continuously for 30 days with a 2 L container of eluent being recycled.

FIG. 15 shows the retention time standard deviation for the nine cycles using a 500 mL volume of eluent. This corresponds to continuously operating for 11 days (24 hours/day) with 2 L of eluent. The retention time standard deviation is less than 1.22% for all analytes.

Example 2

Cation IC Using an Integrated Suppressor and Eluent Generator

An integrated suppressor and eluent generator apparatus for cation IC (FIG. 7) was constructed using machined high density polyethylene hardware to retain the electrodes, membranes and resin. The internal flow dimensions of the suppression chamber were 0.40 cm in diameter and 3.81 cm in length. The internal flow dimensions of the eluent generation were 0.40 cm in diameter and 1.27 cm in length.

The cathode chamber contained a platinum gauze electrode (Unique Wire Weaving Inc, Hillside, N.J.). In contact with the cathode and separating the cathode chamber from the suppression chamber was an anion membrane (Electropure Excellion 1-200 anion membrane, a product of Electropure Inc, Laguna Hills, Calif.). The suppression chamber was filled with anion exchange resin (DOWEX™ 1×4 (200 mesh), a product of The Dow Chemical Company, Midland, Mich.) in the hydroxide form. An anion membrane (Electropure Excellion 1-200 anion membrane, a product of Electropure Inc, Laguna Hills, Calif.) separated the suppression chamber from the eluent generation chamber. The eluent generation chamber was filled with anion exchange resin (DOWEX™ 1×4 (200 mesh), a product of The Dow Chemical Company, Midland, Mich.) in the hydroxide form. Separating the eluent generation chamber from the anode chamber is cation membrane (Electropure Excellion I-100 cation membrane, a product of Electropure Inc, Laguna Hills, Calif.). The anode chamber contained platinum gauze electrodes (Unique Wire Weaving Inc, Hillside, N.J.). The anode is in direct contact with the cation membrane and anode chamber. A Dionex CTC3 cation trap column (not shown in FIG. 1) was placed between the conductivity cell outlet and the eluent generator chamber inlet chamber to trap the analyte cations from the suppressed eluent.

The device of FIG. 7 was tested using a Dionex DX500 Ion Chromatography system (a product of Dionex Corp, Sunnyvale, Calif.) consisting of a GP50 pump, CD25 conductivity detector and a LC30 chromatography oven. An eluent of 20 mN sulfuric acid was pumped at a flow of 1.0 mL/min to a analytical cation exchange column (CG12A/CS12A a product of Dionex Corp., Sunnyvale, Calif.) for separation of the sample cations. An Agilent E3611A DC power supply (Agilent Corp., Santa Clara, Calif.) was used to power the device of FIG. 7 at a constant current of 50 mA (approximately 25V). A peristaltic pump (MASTERFLEX LS, a product of the Cole-Parmer Company, Vernon Hills, Ill.) was used to recycle deionized water at a flow rate of 2.0 mL/min to the anode chamber and then to the cathode chamber and then back to the deionized water container. From the outlet of the analytical column, the eluent was directed to the inlet of the suppression chamber, out of the suppression chamber and to the conductivity cell, out of the conductivity cell and to the trap column and then to the eluent generation chamber. From the outlet of the generation chamber the eluent can be directed to waste (non-recycle mode) or back to the eluent container (recycle mode). FIG. 16 shows a chromatography obtained with the system described above.

Recycling an eluent volume of 120 mL, the retention time trend data in FIG. 17 was obtained. This number of cycles is equivalent to operating the system continuously for 30 days with a 2 L container of eluent being recycled.

Table II show the % RSD of retention times for the analyte cations over the 22 cycles of the sulfuric acid eluent.

TABLE II

% RSD for Retention Times, Cation Chromatography with Integrated Suppression and Eluent Generation (22 cycles)

| Peak | Name | Average RT min | % RSD |
|---|---|---|---|
| 1 | lithium | 3.91 | 0.908 |
| 2 | sodium | 4.75 | 1.00 |
| 3 | ammonium | 5.48 | 1.06 |
| 4 | potassium | 6.90 | 1.12 |
| 5 | magnesium. | 11.5 | 2.99 |
| 6 | calcium | 13.8 | 3.07 |

What is claimed is:

1. A method of using an integrated suppressor and eluent generator apparatus for ion chromatography comprising a suppressor chamber comprising ion exchange material and including an inlet and an outlet, a first electrode chamber comprising a first electrode and including an inlet and an outlet, a second electrode chamber comprising a second electrode and including an inlet and an outlet, an eluent generator chamber comprising flow-through ion exchange material and including an inlet and an outlet, a first barrier preventing significant liquid flow, but permitting transport of ions of only one charge, positive or negative, disposed between said eluent generator chamber and said second electrode chamber, a second barrier preventing significant liquid flow, but permitting transport of ions of only one charge, positive or negative, disposed between said suppressor chamber and said eluent generator chamber, and a third barrier preventing significant liquid flow, but permitting transport of ions of only one charge, positive or negative, disposed between said first electrode chamber and said suppressor chamber, said method comprising (a) flowing an eluent stream comprising separated ionic species of one charge, positive or negative, through said suppression chamber to suppress said eluent, (b) recycling said suppressed eluent from said suppressor chamber, directly or indirectly, to said eluent generator chamber, (c) passing a current between said first and second electrodes through said suppressor chamber and said eluent generator chamber during suppression in step (a) for suppression and eluent generation, and (d) flowing an aqueous rinse solution through said first and second electrode chambers and between them.

2. The method of claim 1 further comprising (e) detecting said separated ionic species after step (a) and prior to recycle to said eluent generator chamber.

3. The method of claim 1 further comprising (e) trapping ions in an ion trap disposed between said suppression chamber and said inlet of said eluent generator chamber.

4. The method of claim 1 further comprising (e) separating a sample prior to step (a) with a chromatography separator, the chromatography separator including ion exchange material and having an inlet and an outlet, said chromatography separator outlet being in fluid communication with said suppressor chamber inlet.

5. The method of claim 1, in which said first and second barriers comprise exchangeable ions of opposite charge.

6. The method of claim 5, in which said third barrier comprises exchangeable ions of a same charge as the second barrier.

7. The method of claim 5, in which the flow-through ion exchange material is selected from the group consisting of a cation exchange material, an anion exchange material, and a combination thereof.

8. The method of claim 1, in which the integrated suppressor and eluent generator apparatus further comprises an ion removal chamber, a fourth barrier preventing significant liquid flow, but permitting transport of ions of only one charge, positive or negative, disposed between said ion removal chamber and said suppressor chamber, said method further comprising
   (e) flowing said suppressed eluent from said suppressor chamber to said ion removal chamber and then to said eluent generator chamber,
   (f) passing said current between said first and second electrodes in step (c) through said suppressor chamber, said ion removal chamber, and said eluent generator chamber, during suppression in step (a) for suppression, removal of ions in said ion removal chamber, and for eluent generation.

9. The method of claim 8 further comprising
   (g) detecting said separated ionic species after step (a) and prior to recycle to said eluent generator chamber.

10. The method of claim 8 in which said third and fourth barriers comprise exchangeable barriers of opposite charge.

11. The method of claim 8 in which said second and fourth barriers comprise exchangeable ions of the same charge.

12. The method of claim 8 in which the ion exchange material in said ion removal chamber comprises exchangeable ions selected from the group consisting of a positive charge, a negative charge, and a mixture of positive and negative charges.

13. The method of claim 8, in which the flow-through ion exchange material is selected from the group consisting of a cation exchange material, an anion exchange material, and a combination thereof.

\* \* \* \* \*